United States Patent [19]

Fowler et al.

[11] Patent Number: 5,914,102
[45] Date of Patent: Jun. 22, 1999

[54] HIGH SPF PERSPIRATION-RESISTANT SUNSCREEN

[75] Inventors: Kevin C. Fowler, Millington, Tenn.; Jonathan Mark Wiggins, Narberth, Pa.

[73] Assignee: Schering-Plough HealthCare Products, Inc., Memphis, Tenn.

[21] Appl. No.: 08/978,823

[22] Filed: Nov. 26, 1997

[51] Int. Cl.$^6$ .............................. A61K 7/47; A61K 7/44; A61K 7/00
[52] U.S. Cl. .............................. 424/59; 424/60; 424/400; 424/401
[58] Field of Search .............................. 424/59, 60, 400, 424/401

[56] References Cited

U.S. PATENT DOCUMENTS 4,606,913  8/1986  Aronson et al. ..................... 424/59
5,585,090  12/1996  Yoshioka et al. .................... 424/59

*Primary Examiner*—Shelley A. Dodson
*Attorney, Agent, or Firm*—Robert A. Franks

[57] ABSTRACT

Sunscreen emulsion formulations of the oil-in-water type containing an aqueous phase, an emulsifier, and an oil phase comprising at least one ultraviolet-absorbing organic compound and hydrophobically treated silica particles, wherein the concentration of said organic compounds is at least about 30 times the concentration of the silica.

17 Claims, No Drawings

HIGH SPF PERSPIRATION-RESISTANT SUNSCREEN

INTRODUCTION TO THE INVENTION

The invention relates to formulations which are applied to skin to reduce the amount of solar ultraviolet radiation received by the skin. More particularly, the invention relates to high SPF formulations containing particulate silica.

It is now generally recognized that exposure to solar radiation can have adverse health consequences, sometimes not appearing until several years following the exposure. Of course, the immediately appearing "sunburn" from an overexposure can itself be a serious acute health problem.

Many products are available to reduce the amount of solar ultraviolet radiation received by the skin during exposure to the sun's rays. Typical product formulations are lotions, creams, ointments or gels containing chemical and/or physical barriers to ultraviolet transmission. These vary considerably in their abilities to protect the skin against the physical and biochemical effects of ultraviolet radiation.

Earlier sunscreening formulations were designed to protect against sunburn from a limited solar exposure period, while transmitting sufficient radiation to permit skin tanning. However, the current focus is on eliminating as much ultraviolet exposure as possible, it being recognized that skin tanning, while esthetically pleasing to some, is a clear indication of tissue damage from overexposure to solar radiation. It has been recently discovered that any amount of unprotected exposure can potentially cause immune system suppression and lead to future health problems, such as skin carcinomas and other dermatological disorders.

The SPF (Sun Protection Factor) rating system has been developed to provide consumer guidance in selecting suitable sunscreens for any given outdoor activity. In general, the SPF number approximately corresponds to the multiple of time during which the properly applied sunscreen will prevent obvious reddening of the skin, over the exposure time that causes unprotected skin to exhibit reddening. Thus, a person should be able to remain in the sun without visible effects for eight times the usual unprotected duration, if an SPF 8 sunscreen formulation has been properly applied. Of course, the duration of unprotected exposure which produces a visible effect on the skin varies from one individual to another, due to differences in their skin cells. Currently popular are high-SPF "sunblocker" products, having SPF values of at least 30.

Most of the commercially available sunscreen formulations are not well suited for use by those engaged in strenuous outdoor activities, such as construction work, gardening, athletic events and many others, due to the tendency for perspiration from the body to interact with the applied formulation. For example, perspiration (or moisture from other sources, including rain) can cause sunscreen active ingredients and other irritating components of the formulation to enter the eyes and cause discomfort. It is also frequently detrimental, particularly in activities such as tennis which require a reliable grip on equipment, to have an applied sunscreen formulation remain lubricious after application or become lubricious when mixed with perspiration or other moisture.

A sunscreen product which has been available for several years, but which does not exhibit disadvantages such as the foregoing, is sold by Schering-Plough HealthCare Products, Inc., Memphis, Tenn. U.S.A. as COPPERTONE® SPORT® SPF 30 lotion. This product contains the active ingredients octyl salicylate, octyl methoxycinnamate and oxybenzone, totaling 17.5 weight percent of the formulation, and is an oil-in-water emulsion formulated with 1.5 weight percent of a fumed silica having a hydrophobic surface treatment. It is thought that the silica serves to immobilize the active agents in the internal phase of the formulation and inhibit their migration under the influence of skin oils and/or external moisture. The product also has a very desirable "dry" feel as it is being applied, quite unlike the very liquid nature of the usual lotion which does not contain particulate ingredients other than those approved for use as sunscreen active ingredients.

There is a need for products having physical attributes as those of the Coppertone Sport SPF 30 product, but which have more predictable formulation behavior and stability characteristics and can be made to have higher SPF values.

SUMMARY OF THE INVENTION

The invention includes sunscreen emulsion formulations of the oil-in-water type containing an aqueous phase, an emulsifier, at least one ultraviolet-absorbing organic compound and hydrophobically treated silica particles, which particles are preferably totally wettable by a 50 volume percent aqueous solution of methanol, wherein the concentration of said organic compounds is at least about 30 times the concentration of the silica. Particularly preferred formulations have concentration ratios of said organic compounds to silica of at least about 40.

DETAILED DESCRIPTION OF THE INVENTION

Names given to chemical substances herein generally are either accepted chemical names, or are trade organization or regulatory agency approved names such as CTFA Adopted Names as listed in J. M. Nikitakis et al., Eds., *CTFA International Cosmetic Ingredient Dictionary, Fourth Ed.*, The Cosmetic, Toiletry and Fragrance Association, Washington, D.C., 1991.

For purposes of the present invention, an "ultraviolet-absorbing organic compound" shall include all of those materials which are regarded as acceptable for use as active sunscreening ingredients. Approval by a regulatory agency is generally required for inclusion of active agents in formulations intended for human contact, and those active agents which have been or are currently approved for sunscreen use in the United States include, without limitation, aminobenzoic acid, avobenzone, cinoxate, diethanolamine methoxycinnamate, digalloyl trioleate, dioxybenzone, ethyl 4-[bis(hydroxypropyl)]aminobenzoate, 2-ethylhexyl 2-cyano-3,3-diphenylacrylate, glyceryl aminobenzoate, homosalate, menthyl anthranilate, octocrylene, octyl methoxycinnamate, octyl salicylate, oxybenzone, padimate A, padimate O, phenylbenzimidazole sulfonic acid, sulisobenzone, and trolamine salicylate. Several other sunscreen active ingredients are accepted for use in other countries. It is typical to use combinations of two or more sunscreen ingredients in a formulation, to achieve higher levels of ultraviolet absorption or to provide useful absorption over a wider range of ultraviolet wavelengths than can be the case with a single active component. Also, mixtures may permit a reduction in the level of certain otherwise desirable agents which have a higher potential for skin irritation or other adverse effects.

It is possible that submicron-sized particles of hydrophobic silica can act to immobilize the sunscreen active agents, such that they will not migrate on the skin under the influence of skin oils, or perspiration or other moisture.

However, an acceptable mechanism for this effect has not yet been proposed, and it is certainly not intended to limit the invention in any manner by a particular theory of operation. Suitable silicas for use in the present invention include submicron silicas which have been chemically treated to provide a hydrophobic surface, such as with organosilicon compounds. These silicas, some of which are described in European Patent Application 0 745 648 published on Dec. 4, 1996, can be obtained from several companies, including Cabot Corporation of Tuscola, Ill. U.S.A., Wacker-Chemie GmbH of Munich, Germany and Degussa AG of Hanau, Germany.

Organosilicon compounds commonly used to provide hydrophobicity include silanes, siloxanes and silazanes. More specifically, commercially available silica products have been reacted with compounds which include trialkylhalosilane, dialkylhalosilane, octaalkylcyclotetrasiloxane, hexaalkyldisilazane, hexaalkyltrisilazane and others.

An example of a useful treated silica is the AEROSIL® R 972 product from Degussa, which is a fumed silica that has been reacted with dimethyidichlorosilane to render the particles hydrophobic. The hydrophobic nature of this material is qualitatively evidenced by a propensity of the treated particles to float (i.e., not be wetted) in water. Silicas are commercially available with other hydrophobic surface treatments, and many of these are suitable for preparing the emulsions of the invention. The Cabot products useful in the invention are sold under the CAB-O-SIL® brand, such as CAB-O-SIL TS610 which is a fumed silica treated with dichlorodimethylsilane The present inventors have determined that the silica must have a certain level of hydrophobicity for optimum results in the invention. A useful test for this property measures the fraction of silica which is wetted (i.e., sinks) in methanol-water solutions of varying concentrations (Method # ACM-125, "Determination of the Methanol Wettability of Hydrophobic Fumed Silicas by the Multipoint Method," Degussa Corporation, Akron, Ohio U.S.A., March 1994): small constant amounts (e.g., 0.200 grams) of silica samples are weighed into graduated 15 milliliter centrifuge tubes; 8.0 milliliters of a methanol test solution is added to each and the tube contents mixed; the tubes are centrifuged; and then the volume of sediment (wetted silica) is read from the tube graduations. The percentage of silica wetted by a particular methanol solution can be determined by comparing its sediment volume with the sediment volume observed when that same silica is contacted with a methanol solution which completely wets the silica, as indicated by the total visual absence of floating silica particles in the centrifuge tube.

In general, to ensure optimum product properties and ease of formulation, it is preferred that the silica should be totally wettable by a 50 volume percent aqueous methanol solution, less than about 25 percent of the particles should be wettable by 35 volume percent methanol, and essentially none (less than about 3 percent of the particles) should be wettable by 30 volume percent methanol. For better results, at least with AEROSIL R 972 produced in Germany, a more preferred silica will be essentially not wetted by either 30 or 35 volume percent aqueous methanol, and will be totally wetted by 50 volume percent methanol; however, some of this silica produced in Japan fails to perform adequately, even though it passes this test. A certain variability in silica hydrophobicity has been observed from batch-to-batch of all commercial products, and acceptable sunscreen formulations can frequently be produced using silica not meeting these specifications, but the production is much more reliable when the silica has the preferred properties.

The silica particles must be quite small, so that they do not occupy the complete volume of the generally micron-sized internal phase of the emulsion. AEROSIL R 972 is claimed by its manufacturer to have an average "primary" particle size of 16 nm, but the material as received shows considerable aggregation; when present in an emulsion formulation, the aggregates probably remain much larger than this primary size. The average aggregate size generally should not exceed about 1 micrometer. Fumed silica most readily can be produced in appropriate particle sizes, but other silicas, such as precipitated silicas and silica aerogel, can also be hydrophobically treated and used in the present invention.

The ratio of sunscreen active agent concentration to silica concentration in the emulsion formulation should be at least about 30, and preferably should be at least about 40.

A combined silica and sunscreen active agent mixture (the "oil" phase), optionally also containing other soluble or dispersible formulation components such as emulsifiers, preservatives, emollients, etc., is emulsified with an aqueous phase, optionally also containing soluble or dispersible formulation components such as emulsifiers, pH buffers, ionic strength adjusters, thickeners, etc. using conventional equipment and techniques. Typical formulations are produced using heated aqueous and/or oil phases, which are combined under conditions of high shear. Shear can be generated by vigorous stirring, subjecting mixtures to high pressures, intersecting high-pressure jets and other techniques which are well known to those skilled in the art. The present invention is not dependent upon any particular formulation technique, it being recognized that the choice of specific formulation components may well make necessary some specific formulation procedure.

Suitable emulsifiers for the invention are those known in the art for producing oil-in-water type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase, and assists with both the formation and the maintenance, or stability, of the emulsion. Sunscreen products are normally lotions, but creams, sprayable liquids and other forms are also useful and may be prepared by a proper choice of components, as is well known in the formulation art.

Most of the widely used oil-in-water emulsifier systems for sunscreen formulations can be used in the invention. Such emulsifiers are exemplified by sorbitol or glycerol esters of long-chain fatty acids (including sorbitan oleate and glyceryl stearate SE), amine salts of alkyl phosphates (including TEA-stearate), amine salts of long-chain fatty acids (including DEA-cetyl phosphate), polymers such as acrylate/alkyl acrylate crosspolymers (including PEMULEN® TR-1 and TR-2, and CARBOPOL® 1342, all sold by B.F. Goodrich Company, Brecksville, Ohio U.S.A), and many others. The choice of an emulsifier is well within ordinary skill in the art and is not a critical aspect of the invention.

The invention will be further described by means of the following examples, which are not intended to limit the invention, as defined by the appended claims, in any manner.

EXAMPLE 1

Sunscreen formulations according to the invention are prepared, using the following ingredients:

| Ingredient | SPF 30 | SPF 48 |
|---|---|---|
| | Grams | |
| Part A | | |
| Water | 57.39 | 54.34 |
| Acrylates/C10–30 alkyl acrylate crosspolymer | 0.38 | 0.38 |
| PEG-8 | 4.23 | 4.23 |
| Preservative | 1.00 | 1.00 |
| Disodium EDTA | 0.01 | 0.01 |
| Part B | | |
| Octyl methoxycinnamate | 7.50 | 7.50 |
| Oxybenzone | 3.00 | 6.00 |
| Octyl salicylate | 5.00 | 5.00 |
| Jojoba oil | 0.10 | 0.10 |
| Vitamin E acetate | 0.10 | 0.10 |
| Aloe vera lipoquinone | 0.10 | 0.10 |
| Homomenthyl salicylate | 8.00 | 8.00 |
| Part C | | |
| Hydrophobic silica (AEROSIL R 972) | 0.55 | 0.60 |
| Part D | | |
| Water | 12.00 | 12.00 |
| DEA-cetyl phosphate | 0.59 | 0.59 |
| Part E | | |
| Fragrance | 0.05 | 0.05 |

A lotion is formulated from these components using the following procedure:

(a) combine and mix all of the Part A ingredients in a vessel, except for the acrylates/C10–30 alkyl acrylate crosspolymer which is sprinkled over the combination and mixed well;

(b) combine and mix all of the Part B ingredients in a vessel and heat to about 57 to 63° C.;

(c) slowly add the Part C ingredient to the mixture of step (b) and mix to thoroughly disperse;

(d) slowly add the step (c) mixture to the step (a) mixture, with high shear mixing using a toothed circular blade, where the teeth alternate between pointing upward and downward, or a propeller having blade tips bent upward, and continue the mixing for 15 minutes;

(e) combine the Part D ingredients in a vessel and heat to about 82–88° C. with mixing to form a clear dispersion;

(f) change the mixer used in forming the step (d) product to a high speed propeller agitator and add to that product the dispersion of step (e) to form a final emulsion, then continue mixing for 3 minutes;

(g) with continued mixing, add to the step (f) product the Part E ingredient and any additional water required to compensate for evaporative losses during the procedure.

EXAMPLE 2

Resistance to mechanical stress degradation of a lotion formulation prepared according to the invention is compared with that of a prior art lotion formulation. The SPF 30 formulation of the preceding example is "A" in the table below, while the "B" formulation is an SPF 30 formulation prepared similarly, but containing 1.50 weight percent of the identical silica (from the same production lot) and the following sunscreen active ingredients: 7.50 weight percent octyl methoxycinnamate; 5.00 weight percent oxybenzone; and 5.00 weight percent octyl salicylate; the concentration ratio of sunscreen active agents to silica is 11.7 in formulation B. The oil phase of the "B" formulation also contains 5.00 weight percent of the emollient octyl palmitate, to approximately match the total "oil phase" contents of the two formulations. This silica is about 3 percent wetted by 30 volume percent aqueous methanol, about 25 percent wetted by 35 volume percent methanol, and is totally wetted by 50 volume percent methanol.

The table gives emulsion droplet sizes, in micrometers, as measured by a laser diffraction technique; 90 percent of the particles in a sample will have droplet sizes below each given value. For each formulation, the "Control" relates to the unstressed emulsion as prepared, the "15 Minutes Mixing" and "30 Minutes Mixing" values are obtained after moderate-speed mixing with a propeller agitator, and the "2.5 Minutes Shaking" and "5 Minutes Shaking" values are obtained following vigorous hand shaking of the formulation in a closed tube.

| Stress | Sample A | Sample B |
|---|---|---|
| Control | 8.32 | 18.6 |
| 15 Minutes Mixing | 9.94 | 38.0 |
| 30 Minutes Mixing | 9.91 | 62.9 |
| 2.5 Minutes Shaking | 12.7 | 43.0 |
| 5 Minutes Shaking | 13.8 | 50.0 |

Production and maintenance of formulations with smaller droplet sizes are preferred. The results above indicate that the sunscreen according to the invention initially has a smaller droplet size, and maintains a smaller droplet size when stressed.

What is claimed is:

1. A perspiration-resistant oil-in-water sunscreen emulsion formulation comprising an aqueous phase, an emulsifier, and an oil phase containing submicron silica particles having a hydrophobic surface and at least one active sunscreen agent, the concentration ratio of sunscreen agents to silica being at least about 30.

2. The formulation of claim 1, wherein the silica particles have average diameters no greater than about 1 micrometers.

3. The formulation of claim 1, wherein the primary silica particles have average diameters about 16 nanometers.

4. The formulation of claim 1, wherein the silica particles are substantially wetted by an aqueous solution containing about 50 volume percent methanol.

5. The formulation of claim 1, wherein no more than about 3 volume percent of the particles are wetted by an aqueous solution containing about 30 volume percent methanol.

6. The formulation of claim 1, wherein no more than about 25 volume percent of the particles are wetted by an aqueous solution containing about 35 volume percent methanol.

7. The formulation of claim 1, wherein the silica particles are substantially wetted by an aqueous solution containing about 50 volume percent methanol, and are essentially not wetted by aqueous solutions containing up to about 35 volume percent methanol.

8. The formulation of claim 1, wherein the concentration ratio of sunscreen agents to silica is at least about 40.

9. The formulation of claim 1, wherein the silica is a fumed silica which has been reacted with dimethyidichlorosilane.

10. A perspiration-resistant oil-in-water sunscreen emulsion formulation comprising an aqueous phase, an emulsifier, and an oil phase containing submicron silica particles having a hydrophobic surface and being wettable by a 50 volume percent aqueous methanol solution, but essentially not wetted by a 30 volume percent aqueous methanol solution, and at least one active sunscreen agent, the concentration ratio of sunscreen agents to silica being at least about 30.

11. The formulation of claim 10, wherein no more than about 25 percent of the silica particles are wetted by a 35 volume percent aqueous methanol solution.

12. The formulation of claim 10, wherein the silica is essentially not wetted by a 35 volume percent aqueous methanol solution.

13. The formulation of claim 10, wherein the concentration ratio of sunscreen agents to silica is at least about 40.

14. The formulation of claim 10, wherein the emulsifier comprises an amine salt of an alkyl phosphate, an acrylate/alkyl acrylate crosspolymer, or a combination thereof.

15. A perspiration-resistant oil-in-water sunscreen emulsion formulation comprising an aqueous phase, an emulsifier comprising at least one of an amine salt of an alkyl phosphate and an acrylate/alkyl acrylate crosspolymer, and an oil phase containing submicron silica particles having a hydrophobic surface and being substantially wettable by a 50 volume percent aqueous methanol solution, but essentially not wetted by a 30 volume percent aqueous methanol solution, and at least one active sunscreen agent, the concentration ratio of sunscreen agents to silica being at least about 40.

16. The formulation of claim 15, wherein the emulsifier comprises a combination of acrylates/C10–30 alkyl acrylate crosspolymer and DEA-cetyl phosphate.

17. The formulation of claim 15, wherein octyl methoxycinnamate, oxybenzone and octyl salicylate are present as active sunscreen agents.

* * * * *